United States Patent [19]

Davidson

[11] Patent Number: 5,415,704
[45] Date of Patent: May 16, 1995

[54] SURFACE HARDENED BIOCOMPATIBLE METALLIC MEDICAL IMPLANTS

[75] Inventor: James A. Davidson, Germantown, Tenn.

[73] Assignee: Smith & Nephew Richards Inc., Memphis, Tenn.

[21] Appl. No.: 120,287

[22] Filed: Sep. 13, 1993

Related U.S. Application Data

[63] Continuation of Ser. No. 832,735, Feb. 7, 1992, abandoned.

[51] Int. Cl.6 .......................... A61F 2/02; C22C 14/00
[52] U.S. Cl. ................... 148/316; 148/238; 420/436; 623/16; 623/18
[58] Field of Search ................ 148/316, 238; 420/436; 623/16, 18

[56] References Cited

U.S. PATENT DOCUMENTS

| | | | |
|---|---|---|---|
| 3,070,468 | 12/1962 | Grant | 148/669 |
| 3,421,890 | 1/1969 | Baumel | 75/171 |
| 3,433,626 | 3/1969 | Bomberger, Jr. et al. | 420/421 |
| 3,471,342 | 10/1969 | Wood | 148/237 |
| 3,643,658 | 2/1972 | Steinemenan | 148/316 |
| 3,933,484 | 1/1976 | Costin | 75/171 |
| 4,012,229 | 3/1977 | Herchenroeder et al. | 75/171 |
| 4,040,129 | 8/1977 | Steinemann et al. | 420/421 |
| 4,124,737 | 11/1978 | Wolfla et al. | 428/640 |
| 4,465,524 | 8/1984 | Dearnaley et al. | 148/316 |
| 4,495,664 | 1/1985 | Blanquaert | 623/23 |
| 4,497,771 | 2/1985 | Spencer et al. | 420/440 |
| 4,582,679 | 4/1986 | Wilson et al. | 420/421 |
| 4,631,082 | 12/1986 | Andrews et al. | 75/235 |
| 4,668,290 | 5/1987 | Wang et al. | 75/235 |
| 4,693,760 | 9/1987 | Sioshansi | 148/421 |
| 4,714,468 | 12/1987 | Wang et al. | 623/16 |
| 4,743,308 | 5/1988 | Sioshansi et al. | 148/239 |
| 4,820,324 | 4/1989 | Gaul et al. | 65/8 |
| 4,846,837 | 7/1989 | Kurze et al. | 205/322 |
| 4,908,072 | 3/1990 | Taki et al. | 148/316 |
| 5,002,731 | 3/1991 | Crook et al. | 420/440 |
| 5,037,438 | 8/1991 | Davidson | 623/18 |
| 5,141,574 | 8/1992 | Takahashi et al. | 148/669 |
| 5,145,530 | 9/1992 | Cassady | 148/669 |
| 5,169,597 | 12/1992 | Davidson et al. | 148/421 |
| 5,178,694 | 1/1993 | Wu et al. | 148/669 |
| 5,227,131 | 7/1993 | Weigand | 420/436 |
| 5,308,412 | 5/1994 | Shetty et al. | 148/238 |

FOREIGN PATENT DOCUMENTS

| | | |
|---|---|---|
| 0213781 | 3/1987 | European Pat. Off. |
| 0359446 | 3/1990 | European Pat. Off. |
| 0437079 | 7/1991 | European Pat. Off. |
| 0444280 | 9/1991 | European Pat. Off. |
| 2811603 | 9/1979 | Germany |
| 9007016 | 6/1990 | WIPO .......................... C22C 14/00 |

OTHER PUBLICATIONS

Rudinger et al., in Titanium Science & Technology (eds) Jaffee et al. vol. 4, Met. Soc. Aime, Plenum, N.Y. 1973 pp. 2555-2571.

(List continued on next page.)

Primary Examiner—Upendra Roy
Attorney, Agent, or Firm—Pravel Hewitt Kimball & Krieger

[57] ABSTRACT

This invention provides surface hardened, abrasion resistant high strength, biocompatible metal medical implants, in particular, titanium alloy implants which do not include any elements which have been shown or suggested as having short term or long term potential adverse effect from a standpoint of biocompatibility. Further, the invention provides methods of strengthening and hardening the surfaces of other titanium, zirconium, and cobalt-based alloy implants with small concentrations of a metal solute such as zirconium, yttrium, tantalum, aluminum, silicon, chromium, or thorium via internal oxidation or nitridation. Alternatively, nitrogen, oxygen, or carbon can be diffused directly into the surface of the implants by interstitial hardening to further increase the surface abrasion resistance of these internally oxidized or internally nitridized implant metal or metal alloys.

16 Claims, 1 Drawing Sheet

OTHER PUBLICATIONS

"Strengthening of Niobium–Zirconium Alloys by Internal Oxidation," D. J. Rowcliffe, et al., *Oxide Dispersion Strengthening*, Ed: G. S. Ansell, T. D. Cooper & F. V. Lenel, Gordon & Branch, N.Y. (1968).

Rüdinger, et al., Ti–Science & Technology, ed. Jaffee, et al., Plenum, N.Y. 1973, pp. 2555–2571.

Swisher, J. H., "Internal Oxidation," Paper presented at a Seminar of the American Society for Metals, Oct. 17–18, 1970, pp. 235–267.

Thull, R.; Medical Prog. Through Tech., 16 (Nov. 1990) 225–34.

Streicher, et al., Biomaterials 12 (Mar. 1991) 125–29.

Sutow, et al., Jour. Dent. Research 64 (1985) 842–47.

SURFACE HARDENED BIOCOMPATIBLE METALLIC MEDICAL IMPLANTS

This is a continuation of application Ser. No. 07/832,735, filed Feb. 7, 1992, abandoned.

BACKGROUND

1. Field of the Invention

This invention relates to surface hardening of biocompatible metallic metals and alloys, suitable for use as material for a medical implant, including in particular, niobium, titanium, and zirconium based alloys which do not include any elements which have been shown or suggested as having short term or long term potential adverse biological effects. More specifically, this invention relates to medical implants made of these surface-hardened alloys with improved resistance to micro-fretting wear and surface abrasion.

2. Description of the Related Art

The most common materials used for load-bearing medical implants such as orthopedic or cardiovascular implants, are metallic alloys, ceramics, and composites formed from biocompatible polymers and various reinforcing materials.

Metals and metal alloys such as stainless steel, Co—Cr—Mo alloy, titanium, and titanium alloys have been used successfully for many years as implant materials, particularly for orthopedic applications. These materials have the requisite strength characteristics needed for such implants but are susceptible to fretting, wear, and corrosion in the body unless treated to reduce these effects. Particulates produced by joint articulation processes or micromotion between assembled devices tend to cause accelerated wear of prosthetic joints and trauma devices.

Further, concern has been raised about potential abrasion between implant metals and adjacent bone and bone cement. This abrasion creates particulates which are associated with adverse cellular response, including bone cell death and eventual loosening of the implant and subsequent revision.

To prevent micro-fretting of the implant surface, the surface may be coated with an amorphous diamond-like carbon coating or a ceramic-like coating, such as titanium nitride or titanium carbide, using chemical or plasma vapor deposition techniques to provide a hard, impervious, smooth surface coating. These coatings are especially useful if the prosthesis is subjected to conditions of wear, such as, for instance, in the case of bearing surfaces of knee or hip prostheses, or between screws and bone plates or modular implants. For the case of orthopedic implant bearing surfaces, bone cement fragments can abrade these relatively thin (up to about 5 microns) surface coatings with time and create hard, abrasion products from these coatings which in turn further accelerate abrasion and wear of the softer underlying metal substrate.

Methods for providing amorphous diamond-like carbon coatings are known in the art and are disclosed in, for example, EPO patent application 302 717 A1 to Ion Tech and Chemical Abstract 43655P, Vol. 101 describing Japan Kokai 59/851 to Sumitomo Electric, all of which are incorporated by reference herein as though fully set forth.

With orthopaedic and cardiovascular implants being implanted in younger people and remaining in the human body for longer periods of time, there is a need for an implant material with requisite strength and high abrasion resistance which minimizes the production of abrasive particles from surface abrasion effects.

SUMMARY OF THE INVENTION

The invention provides novel hardened metallic implants with high abrasion resistance and methods for increasing implant abrasion resistance without the use of a hard deposited overlay ceramic-like coating. In one embodiment of the invention implants internal oxidation or nitridation is used to harden the implants' surfaces. While a minimal external surface oxide or nitride scale may form on these hardened implants, surface strengthening is primarily due to dispersion strengthening by internal oxidation or nitridization just below the implant's surface. Thus, there is no significant hard external scale formed which may spall off or produce abrasion products to damage the implant surface or cause undesirable biological effects.

In another embodiment, the invention also provides for the additional hardening of the implant surface with interstitial diffusion of oxygen, nitrogen, or carbon. This latter method is used on implants which have previously been treated with an internal oxidation or nitridization treatment. A lower diffusion hardening temperature can be utilized which will not affect the previously internally oxidized or nitrided benefits.

The invention oxidizing or nitriding method of surface hardening implant metals provides a fine oxide or nitride dispersion within the metal surface without a significant surface scale so that the implant essentially retains its metallic appearance.

Standard nitriding, oxidizing, and carbonizing treatments for metals are available and known to persons skilled in the art. These methods use plasma, fluidized beds, molten salts, or nitrogen, oxygen, or carbon-containing gaseous environments at elevated temperatures to perform surface treatments. In these methods, diffusion of nitrogen, carbon, and oxygen into the metallic implant and the subsurface nucleation of nitrides, carbides, or oxides increases hardness and strengthens the metal to depths of 50 microns or more depending on gas concentration, time, temperature, and alloy composition. However, the formation of nitrides or carbides in chromium-containing metals occurs via formation with the chromium. Thus, local depletion of chromium can occur in the matrix adjacent to the nitride or carbide particle and reduce corrosion resistance. Oxygen diffusion hardening of titanium alloys promotes an undesirable, weaker alpha case on the surface. Internal oxidation or nitridization avoids introducing these limitations of corrosion resistance and loss of strength.

While surface hardening by conventional oxygen, nitrogen, or carbon diffusion forms no significant external nitride or carbide scale, if done at sufficiently low partial pressures of these diffusing species, the metallic implant's surface hardness can exceed 50 Rockwell C in the case of certain titanium alloys, significantly higher than for the untreated alloy, which can vary up to about 40 Rockwell C depending on the metal and the heat-treated condition of the metal. Further, conventional diffusion hardening surface treatments can significantly improve surface abrasion and fretting resistance for titanium alloys and stainless steels. Surface hardening by diffusion may be more effective with some metals than others, depending on the rate of diffusion in the particular metal, and the stability of the microstructure at the diffusion hardening temperature. Further, diffusing species such as nitrogen or carbon may react with chromium in cobalt alloys or stainless steel, rendering them less corrosion resistant. Internal oxidation can eliminate the latter concern.

The internal oxidation or nitridization process is applicable to almost any metallic implant. To produce the invention hardened implant, a low concentration of a more readily oxidizable (or nitridable) metal solute is added to the metallic implant's alloy composition, so that the internal oxidation (or nitridization) process strengthens and hardens the surface via reaction of this specific solute with diffusing oxygen (or nitrogen). This is in contrast to conventional diffusion hardening methods described above. Selection of a suitable metal solute for internal oxidation or nitridization is based upon the thermodynamics of the process. Specifically, the more negative the value is for the free energy of formation (i.e., $\Delta G°$) for a particular metal oxide (e.g. $Ta_2O_5$), the greater the tendency (i.e. thermodynamic driving force) to form the oxide at a given temperature within the metal or alloy.

For internal oxidation surface hardening and strengthening, the depth of the internally oxidized zone, the oxide particle size, and the strength of the alloy depend on the oxidizable solute's concentration, the concentration of oxygen in the oxidizing environment, the oxidation temperature, and the oxidation time. Because the strength of the surface is increased, the implant's fatigue strength in tension bending will also increase, as well as its surface hardness and subsequent abrasion resistance.

While the invention surface hardened implants possess a relatively high strength, the usefulness of these hardening processes is not limited to treating implants in load-bearing applications. Because of its abrasion resistance, enhanced fatigue strength, and tension bending strength, the hardened implants can be used in many types of implants including, but not limited to, hip joints, knee joints, compression hip screws, tooth implants, skull plates, fracture plates, intramedullary rods, staples, bone screws, cardiovascular implants, such as heart valves and artificial heart and ventricular assist devices, and other implants.

DETAILED DESCRIPTION OF THE PREFERRED EMBODIMENTS

I. The Implant Metals

Figure 1:
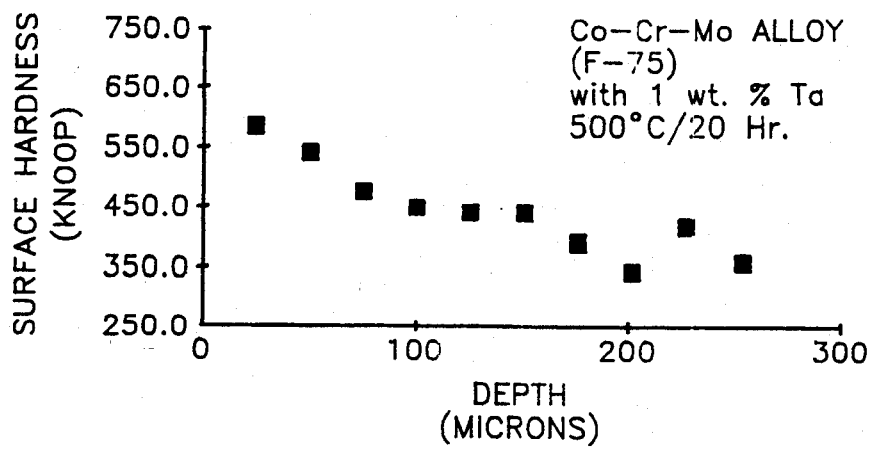
FIG. 1 is a surface hardness vs. depth curve (from the surface) for a Co—Cr—Mo alloy coupon alloyed with 1 wt. % tantalum which has been surface hardened by internal oxidation at a temperature of 500° C. for 20 hours.

The invention provides surface hardened, abrasion resistant medical implants. The hardening methods may be applied to all currently used implant metals include AISI 316L stainless steel (i.e. Fe—Cr—Ni—Mo), Co—Cr—Mo (F75 or F799) and Ti-6Al-4V, and those alloys that may be contemplated as useful. While the methods for producing the invention abrasion resistant metallic implants may be applied to almost any metal or alloy used to fabricate implants, the Co—Cr—Mo and titanium alloys are preferred in the present invention. Consequently, much of the description will discuss titanium alloy implants, it being understood that other alloys may also be similarly processed by the invention methods to produce the invention surface hardened implants. Examples of preferred titanium alloys include Ti-6Al-4V, beta titanium alloys, Ti—Mo, Ti—Al—Nb, TiV and Ti—Fe. Newer, more biocompatible titanium alloy compositions with lower elastic moduli such as Ti—Zr, Ti—Nb—Zr and Ti—Nb, are also capable of internal oxidation, as are zirconium and niobium based alloys. Examples of such compositions may be found in our application U.S. Ser. No. 07/454,181, filed Jan. 28, 1991, which is fully incorporated by reference. Other metals and metal alloys that may be employed include, but are not limited to, zirconium and zirconium alloys such as Zr—Nb, for example, and stainless steels, such as, for example, stainless steel 316L (Fe—Cr—Ni—Mo).

The most preferred biocompatible, low-modulus titanium alloy implants may be produced by combining, as commercially pure components, titanium, niobium, and zirconium in the appropriate proportions. The titanium alloys (depending on the alloying constituents) may further contain concentrations of another metal (typically less than 2 wt. %), such as tantalum, yttrium, thorium, chromium, aluminum, and the like, for purposes of internal oxidation. Ti—Nb alloys may contain zirconium, aluminum, yttrium, hafnium, or tantalum in concentrations less than about 2 wt. % for the same purpose. Zirconium or zirconium alloys may contain less than about 2 wt. % tantalum, yttrium, thorium, or aluminum for this purpose. Cobalt alloys and stainless steels may contain less then about 2 wt. tantalum, aluminum, and yttrium for this purpose.

One preferred alloy contains titanium as the major component comprising about 74 wt. % of the alloy in combination with about 13 wt. % of zirconium and 13 wt. % niobium. Less than about 2 wt. % of another metal such as tantalum or aluminum is added to replace the same amount of titanium, or zirconium, or to a lesser degree, niobium (since niobium concentration is important to establish a low modulus). The other group of preferred alloys also contains titanium as the major component, comprising about 84 to 87 wt. % of the alloy, in combination with about 13-17 wt. % niobium, and less than about 2 wt. % tantalum, yttrium, hafnium, thorium, aluminum, and chromium. The additional metal added preferably replaces the same amount of titanium or to a lesser degree niobium. The most preferred biocompatible low modulus alloys include Ti-13Nb-13Zr and 1% Ta; and, Ti-15Nb with 1% Ta.

The methods of making and using implants of titanium, niobium (and optionally tantalum as a substitute for niobium) and optionally zirconium or zirconium alloy (and optionally tantalum, yttrium, or aluminum as a substitute for zirconium) is described in our copending application U.S. Ser. No. 07/454,181, filed Jan. 28, 1991, referred to above. The machining, casting or forging of the alloys into the desired implant shape may be carried out by any of conventional methods used for titanium or zirconium alloys.

Implants fabricated from the titanium alloys may be supplied with a sintered porous bead or wire or plasma-sprayed coating of titanium alloy of the same or different composition, or even pure titanium, to allow stabilization of the implant in the skeletal structure of the patient after implantation by bone ingrowth into the porous structure. Similarly, zirconium or zirconium alloys may be supplied with the similar porous coatings of zirconium or zirconium alloy. Such porous structures are occasionally attached to the implant surface by sintering. Similarly, cobalt alloys may be supplied with a porous metal coating. Because sintering of porous coating is preferred at temperatures above 1000° C., the mechanical properties of titanium alloys can change significantly due to substantial grain growth, phase changes, and other metallurgical factors arising from the sintering process. Thus, for example, after sintering to attach the porous coating, additional heat treatments are desired to restore mechanical properties. To avoid these potential restrictions, the implant metal or alloy may be porous coated using plasma spray methods in which minimal heating occurs to the base material.

While the preferred titanium alloys themselves provide a non-toxic material suitable for orthopedic, cardiovascular, or other medical implants, it is desirable, for other reasons, such as micro-fretting against bone or polyethylene bearing surfaces, or microfretting, to harden the surface of an implant fabricated from these alloys. Furthermore, in the case of non-titanium alloys, such as the stainless steels or cobalt alloys, surface hardening may be desirable for both increasing fatigue strength and the reduction of micro-fretting or abrasive wear.

II. Hardening and Strengthening the Alloy Surface

The invention provides methods to strengthen and harden an alloy's surface and includes (1) an internal oxidation process which includes adding a low concentration of a more readily oxidizable solute such as yttrium, niobium, tantalum, zirconium, thorium, hafnium, chromium, or aluminum to the alloy, and oxidizing a portion of the solute that is found immediately beneath the metal surface; (2) an internal nitridization process which includes adding low levels of a relatively more nitridable solute such as zirconium, silicon or thorium to the alloy and nitriding a portion of this solute that is found just below the metal surface; and (3) an additional interstitial diffusion strengthening process using nitrogen, oxygen, or carbon. For the internal oxidation and nitridization processes, the particular oxidizable or nitridable solute selected will vary, depending upon the particular metal or metal alloy composition of the implant. Each of these three methods will be discussed in turn.

Internal Oxidation

In the internal oxidation process, a small quantity of a "more readily oxidizable solute" is added to the alloy from which the implant is to be fabricated. By more readily oxidizable solute, we mean one that oxidizes more readily than the other constituent metals of the alloy with which the solute is admixed or alloyed. During controlled oxidation, oxygen diffuses into the implant's surface leading to the formation of a fine dispersion of solute oxide particles on and immediately below the alloy surface. The depth of this internally oxidized zone, the oxide particle size, and hardening and substrate strengthening of the surface depends on the solute concentration, the concentration of oxygen in the oxidizing environment, the oxidation temperature, and the oxidation time. Because both the hardness and strength at the surface is increased, the fatigue strength will also increase. For example, Rowcliffe, et al. (*Oxide Dispersion Strengthening*, Ansell et al., ed., Gordon and Breach, N.Y., "Strengthening of Niobium-Zirconium Alloys by Internal Oxidation," 1968) have shown that the yield and ultimate tensile strength of Nb-1Zr alloy can double by internal oxidation. Their research was, however, aimed at improving high temperature creep resistance of the alloy and there is no teaching or suggestion of the use of such a method to produce a surface-hardened medical implant for improved wear and abrasion resistance.

In the case of titanium or Ti—Nb alloys, tantalum may be added as a solute, because tantalum is more reactive with oxygen (lower free energy of formation) than either titanium or niobium. Thus, it is possible to internally oxidize the alloy without oxidizing niobium or titanium if the concentration of oxygen (partial pressure of oxygen) is less than that required to form niobium or titanium oxides. Similarly, for Ti—Nb—Zr or Zr—Nb alloys with tantalum added as a solute, the concentration of oxygen is less than that required to form titanium, niobium, or zirconium oxides. Additionally, when tantalum is added as a solute, to Co—Cr—Mo alloys, then the more oxidizable tantalum causes internal oxidation of the alloy. Table 1 is a list of published standard free energies of formation ($\Delta G°$) for various titanium, niobium, zirconium, tantalum, aluminum, yttrium, and other oxides. The more negative the $\Delta G°$ value, the greater the tendency (i.e. thermodynamic driving force) to form the oxide at a given temperature, $T(°K)$.

TABLE 1

$\Delta G° = A + BT_{log}T + CT$

| Oxide | A | B | C | $-\Delta G$ (K cal.) 600° | 800° |
|---|---|---|---|---|---|
| Al$_2$O$_3$ | −405 | 4 | −92 | 475 | 495 |
| Cr$_2$O$_3$ | −268 | 1 | −62 | 323 | 333 |
| CoO | — | — | — | 261 | 275 |
| HfO$_2$ | −268 | 2 | −78 | 334 | 350 |
| MoO$_2$ | −141 | 5 | −56 | 181 | 192 |
| NiO | −58 | — | −24 | 80 | 84 |
| NbO | — | — | — | 119 | 130 |
| SiO$_2$ | −215 | — | −42 | 253 | 261 |
| Ta$_2$O$_5$ | −491 | 31 | −168 | 644 | 666 |
| ThO$_2$ | −293 | 2 | −48 | 332 | 342 |
| TiO$_2$ | — | — | — | 280 | 290 |
| TiO | −122 | 1 | −21 | 141 | 144 |
| VO | — | — | — | 137 | 145 |
| Y$_2$O$_3$ | −420 | — | −66 | 479 | 493 |
| ZrO$_2$ | −260 | 5 | −60 | 301 | 313 |

Thus, those skilled in the art can appreciate that the low-modulus titanium-niobium and titanium-niobium-zirconium alloys described in U.S. Ser. No. 07/454,181 and other titanium, cobalt, and zirconium alloys described above can be internally oxidized by the presence of small quantities of relatively more oxidizable solutes such as yttrium, chromium, aluminum, hafnium, and tantalum. Tantalum and aluminum can be used for internally oxidizing Ti—Nb—Zr alloys as their $\Delta G°$ is more negative than even that of zirconium or niobium. However, based on biological factors, aluminum is not preferred over tantalum. These biological factors are partially mitigated because the aluminum near the surface of the implant converts to inert aluminum oxide so that the presence of aluminum will not be as potentially detrimental as if aluminum metal were present in the bulk alloy. The alloys that may be internally oxidized via the presence in the alloy of small amounts (in parentheses) of zirconium, tantalum, or aluminum include, but are not limited to, Ti—Nb—Zr—(Ta), Ti—Nb—(Zr), Ti—Nb—(Ta), and Ti—Nb—(Cr), Ti—Al-V-(Ta), Co—Cr—Mo—(Ta), and 316L stainless steel (Ta). Other combinations are also possible based on relative differences in $\Delta G°$ between the preferred solute and other alloy constituents.

In the internal oxidation process, the depth of internal oxidation (flat plate surface) from the surface (X) for a given period of time (t) is represented by the following equation.

$$X = [2N_O^{(s)} D_O t / \nu N_b^{(0)}]^{\frac{1}{2}}$$

where: $N_O^{(s)}$ is the concentration of oxygen at the surface (less than that required to oxidize either the titanium or niobium base alloy, for example if tantalum is added as the solute); $D_o$ is the rate of diffusion of oxygen into the surface; v is the stoichiometric value (ratio) of oxidizing solute species to oxygen (i.e., v=2 for $ZrO_2$); and $N_b^{(0)}$ is the concentration of the solute which is being internally oxidized (i.e., chromium, aluminum, yttrium, or tantalum, and the like).

For internal oxidation, the depth increases with decreasing concentration of solute. The value $N_o^{(s)}$ is related, by a reaction rate constant, to the square root of the partial pressure of oxygen.

To optimize the strengthening effect of the internal oxidation process, the advancing front of diffusing oxygen should progress rapidly. This results in more nucleation and less growth of internal oxide particles, and therefore smaller, more effective particles. Relatively lower oxidation temperatures are also preferred to minimize particle growth, but presents a trade-off with the rate of oxygen diffusion. Thus, the partial pressure of oxygen and the solute concentration should be maximized (preferably less than about 2 wt. %). Various times and temperatures are possible and can be optimized experimentally.

To internally oxidize a particular alloy implant containing a more readily oxidizable added solute such as tantalum, yttrium, aluminum, or zirconium, the alloy implant is packed in a mixture of a metal and its oxide whereby the metal selected for the packing mixture is the next most readily oxidizable solute compared to the added metal solute (e.g. tantalum and zirconium). Oxygen is evacuated from the implants environment and residual oxygen is scavenged by, for example, resistance heating a zirconium or tantalum wire in the evacuated environment. [This is called "getting" the oxygen to a sufficiently initial low level.]. Upon heating the alloy implant, the metal oxide in the packing and the metal in the packing attain an equilibrium which produces the required low level of oxygen concentration (partial pressure) in the system, sufficient to react primarily with the low concentration of more readily oxidizable metal solute present in the implant and to thereby internally oxidize the metal implant's surface.

For example, to internally oxidize a Ti-6Al-4V implant with a tantalum solute, the implant is evacuated in a packed mixture of aluminum and aluminum oxide, since aluminum is the most readily oxidizable metal next to tantalum. Any remaining oxygen in the evacuated system is reduced by resistance heating a zirconium or tantalum wire in the evacuated environment. Upon heating to about 500° C.-1200° C. for up to about 100 hours (depending upon the desired depth and hardening), the aluminum metal and aluminum oxide establish an oxygen partial pressure (or $N_O^{(s)}$) sufficient to produce oxidation of the tantalum solute by diffusion of oxygen into the alloy surface, but without causing the titanium, aluminum, or vanadium in the alloy to form a significant external oxide scale. For this case, it is more desirable to establish the partial pressure of oxygen close to $10^{-6}$ torr because levels near $10^{-5}$ torr tend to produce aluminum monoxide (AlO) near the surface. At oxygen pressures less than $10^{-6}$ torr, the strengthening effect is less pronounced (i.e. more growth vs. nucleation of the internal oxide particles) due to lower levels of oxygen and slower penetration (diffusion) rates of oxygen into the surface. Oxidation depth should preferably be less than about 200 microns, most preferably less that about 100 microns in order to minimize particle size (less than about 150 angstroms), processing time, and temperature, and to optimize hardness and strength.

The preferred internal surface strengthened metallic implants having excellent biocompatibility include those produced by the internal oxidation of shaped Ti—Nb alloys using small concentrations of zirconium, yttrium, or tantalum (i.e. Ti—Nb—Zr, Ti—Nb—Y, or Ti—Nb—Ta), or internal oxidation of Ti—Nb—Zr implants or zirconium or zirconium implants using small concentrations (less than about 2 wt. %) of tantalum (i.e. Ti—Nb—Zr—Ta or Zr—Ta) or yttrium. Additionally, aluminum solute levels less than about 2 wt. % would be effective for internally oxidizing these implants.

Internal Nitridization

As an alternative to internal oxidation, internal nitridization can be performed by adding low levels (less than about 2 wt. %) of a solute more nitridable than the base alloy constituents. By a "more nitridable solute," we mean one that nitrides more readily than the other constituent metals of the alloy with which it is admixed or alloyed. In the case of the titanium alloys, solutes such as zirconium, silicon, or thorium may be added. The titanium alloys (with solutes for internal nitridization in parentheses) suitable for internal nitridization via the presence of small amounts (i.e. less than 2 wt. %) of silicon, thorium, or zirconium include, but are not limited to, Ti—Nb—(Si), Ti—Nb—(Th), and Ti—Nb—(Zr). Zirconium alloys should contain less that about 2 wt. % of silicon or thorium, and cobalt alloys and 316L stainless steel should contain less than about 2 wt. % of thorium, tantalum, aluminum, silicon or zirconium. Table 2 is a list of the published standard free energies of formation ($\Delta G°$) for the nitrides of these elements:

TABLE 2

| | $\Delta G°$, Kcal, = A + BTlogT + CT | | | |
|---|---|---|---|---|
| Nitride | A (K Cal) | B | C | $-\Delta G$ at 800° C. |
| TiN | −160 | — | −45 | 210 |
| NbN | −114 (est) | — | −50(est) | 169 |
| ZrN | −175 | — | −46 | 226 |
| TaN | −117 | 14 | −80 | 170 |
| $Cr_2N$ | −52 | 11 | −66 | 105 |
| AlN | −154 | — | −44 | 202 |
| $Si_3N_4$ | −177 | 6 | −97 | 264 |
| $Th_3N_4$ | −310 | — | −90 | 409 |
| $Mo_2N$ | −34 | 9.2 | −58 | 80 |

One skilled in the art can see that unlike the free energy of formation of the oxide (see Table 1), tantalum, chromium, and aluminum would not tend to effectively form internal nitride particles as compared to the titanium or niobium base metal alloy which have similar free energy of formation values. For example, even zirconium has only a slightly more negative ΔG° than titanium or niobium. Thus, for internal nitridization of a Ti—Nb low modulus alloy, small concentrations (less than about 2 wt. %) of either silicon or thorium are preferred because of their significantly more negative levels of free energy of formation. A small concentration of zirconium is also effective, but to a lesser degree.

Similar internal nitridization relationships apply as for internal oxidation. However, the packing material used to establish the appropriate concentration (partial pressure) of nitrogen would be a combination of the metal and metal nitride of the most nitridable (next to that of the solute) metal constituent in the alloy.

It should be noted that for both internal nitridation and oxidation, a substantial portion of the respective solute added that occurs at the implant's surface will undergo nitridization or oxidation. Solute concentrations are preferably less than about 2 wt. %. While more solute may be added, surface hardening will not be as effective therefore such addition is not preferred.

Interstitial Diffusion Strengthening

Another method which may be used to improve the surface abrasion resistance of metallic implants, especially the preferred titanium implants such as Ti—Nb—Zr, Ti—Nb, Ti—Nb—Zr—Ta, Ti—Nb—Ta and zirconium and zirconium alloys, is "interstitial diffusion" strengthening of the surface with oxygen, nitrogen, or carbon. Treatments for interstitial diffusion strengthening of metals generally use gaseous or liquid nitrogen or carbon-containing environments or gaseous environments, including fluidized beds, or similar oxygen-containing environments, at elevated temperatures, and are known to those skilled in the art. Diffusion strengthening to depths of less than 100 microns are usually sufficient. In the interstitial diffusion strengthening process, oxygen, nitrogen, and carbon concentrations are kept sufficiently low so that there is no significant formation of an external oxide nitride or carbide scale so that an essentially metallic-type appearance remains on the surface. The surface hardness of a typical 33 Rockwell C hardness titanium alloy when so treated can exceed 60 Rockwell C hardness and can also significantly improve surface abrasion and fretting resistance.

While the general interstitial diffusion hardening process using oxygen, nitrogen, and carbon is used commercially and is well known to those of skill in the art, its application to Ti—Nb, Ti—Nb—Zr, zirconium, Ti-6Al-4V, Co—Cr—Mo, and other medical implant metals capable of internal oxidation or internal nitridization is novel. This diffusion hardening process can be applied to the preferred titanium alloy, zirconium alloy, cobalt alloy, and stainless steel compositions, whether or not these alloy compositions have received a previous internal oxidation or internal nitridization treatment, to achieve additional benefits.

It should be noted that the internal oxidation and interstitial diffusion hardening methods can be controlled to minimize or eliminate the formation of an external scale-type coating. Therefore, the hardened implants surface may, with little or no additional surface treatment, be coated with, for example, amorphous diamond-like carbon, pyrolytic carbon, TiN, TiC, and oxide coatings and the like, which are physical or chemical vapor deposited, for further improved abrasion resistance, if desired. The hardening treatment of any of the methods described in this specification would improve the attachment strength of these coatings.

The following examples are intended to illustrate the invention as described above and claimed hereafter and are not intended to limit the scope of the invention in any way.

Example 1

A coupon formed of Co—Cr—Mo alloyed with about 1 wt. % of tantalum was placed in a tube and packed with chromium and chromium oxide. The tube was evacuated to remove essentially all oxygen and sealed. The tube was then placed in a furnace and heated to a temperature in the range 500 to 800° C. for a certain time period as indicated in Table 1 below. The tube was then allowed to cool to room temperature. This procedure was also applied to a Ti-13Nb-13Zr alloy (packed with zirconium and $ZrO_2$) and a Ti-6Al-4V alloy (packed with aluminum and $Al_2O_3$), each containing about 1 wt. % tantalum, both of which were heated to the temperatures and for the time periods indicated in Table 3 below. The bulk hardness, surface hardness, and hardness gradient depths for each of the three alloys after internal oxidation at the indicated conditions are shown in Table 3.

TABLE 3

Summary of internal Oxidation Surface Hardening Results For Selected Implant Materials

| Material | Internal Oxidation Parameters | | Bulk Hardness (Knoop) | Surface Hardness (Knoop) | Hardness Gradient Depth (Micron) |
|---|---|---|---|---|---|
| | Temp (C.°) | Time (Hrs.) | | | |
| Co—Cr—Mo | 500 | 1 | 300 | 350 | 50 |
| (F-75) | 500 | 6 | 340 | 550 | 150 |
| w/1 wt. % Ta | 500* | 20 | 340 | 600 | 200 |
| | 600 | 1 | 310 | 650 | 200 |
| | 600 | 6 | 300 | 500 | 250 |
| | 600 | 20 | 310 | 650 | 300 |
| | 700 | 1 | 300 | 600 | 200 |
| | 700 | 20 | 340 | 600 | 250 |
| | 800 | 1 | 280 | 450 | 100 |
| | 800 | 6 | 350 | 500 | 200 |
| Ti-13Nb-13Zr | 700* | 20 | 225 | 400 | 150 |
| w/1 wt. % Ta | 700 | 100 | 225 | 425 | 200 |
| | 800 | 1 | 215 | 300 | 250 |
| | 800 | 6 | 240 | 350 | >300 |
| Ti-6Al-4V | 800 | 1 | 275 | 375 | 100 |
| w/1 wt. % Ta | 800* | 20 | 280 | 375 | 150 |

Figure 2:
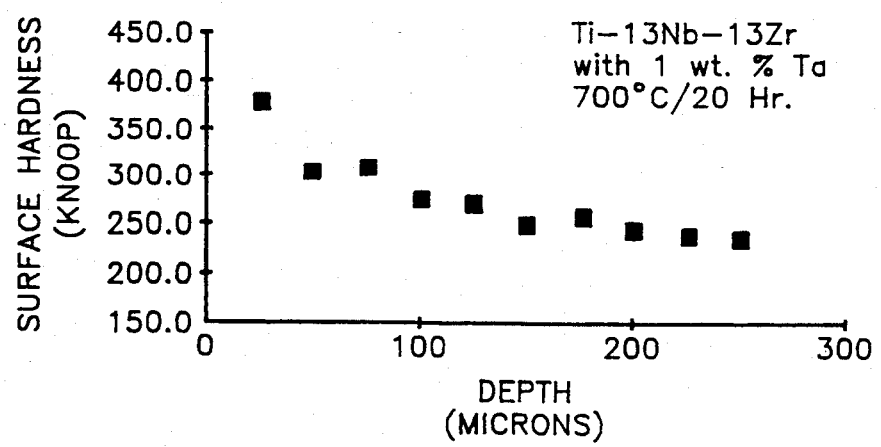
FIG. 2 is a surface hardness vs. depth curve for a Ti-13Nb-13Zr alloy coupon alloyed with 1 wt. % tantalum which has been surface hardened by internal oxidation at a temperature of 700° C. for 20 hours.
Figure 3:
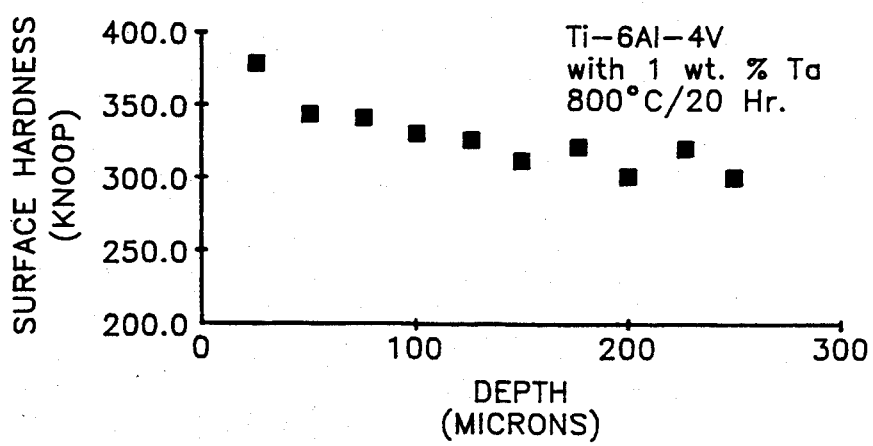
FIG. 3 is a surface hardness vs. depth curve for a Ti-6Al-4V alloy coupon alloyed with 1 wt. % tantalum which has been surface hardened by internal oxidation at a temperature of 800° C. for 20 hours.

FIGS. 1–3 represent the surface hardness vs. depth curves for the alloy materials marked with asterisks as shown in Table 3. Specifically, FIG. 1 is the surface hardness vs. depth curve for a Co—Cr—Mo alloy containing 1 wt. % Ta which has been heated to 500° C. for 20 hours. FIG. 2 represents the surface hardness vs. depth curve for a Ti-13Nb-13Zr alloy containing 1 wt. % Ta which has been heated to 700° C. for 20 hours. FIG. 3 represents the surface hardness vs. depth curve for a Ti-6Al-4v alloy containing 1 wt. % Ta which has been heated to 800° C. for 20 hours. The peak hardness values given in Table 3 are not necessarily as great as that produced by the curves shown in FIG. 1–3. Extrapolation of these curves suggest a still higher hardness at the immediate surface.

While it is clear that a chemical element of the Periodic Table that is a metal is a pure metal, alloys of metallic elements are also referred to as "metals," in the sense that they are metallic rather than ceramic organic, etc. Therefore, in the specification and claims when reference is made to a "metal implant," this includes an implant fabricated from a metal alloy as opposed to a ceramic or polymer or composite. Further, in the specification and claims when an alloy is combined with a metal solute, it forms a "solute-containing alloy." Thus, when an alloy of a given composition, commercially available or specially made, is specified, its composition does not include the metal solute, unless so specified. Therefore, in the claims the metal implants composition is specified in terms of (1) a metal composition and (b) the metal solute subsequently added to then make the solute-containing alloy from which the implant body is fabricated.

The invention has been described with reference to its preferred embodiments. After studying this disclosure, a person of skill in the art may appreciate changes and modifications that are within the spirit of the invention as disclosed above and within the scope of the claims herebelow.

I claim:

1. A surface hardened metallic medical implant, the implant comprising:
   a surface hardened metallic alloy implant body with surface hardness greater than about 40 Rockwell C, the alloy comprising metallic elements and the hardened surface produced by a process comprising:
   (i) selecting a metallic alloy containing less than about 2 wt. % of a metal solute more readily oxidizable than and different than other elements of the metallic alloy implant body;
   (ii) hardening the surface of the implant body by internal oxidation of a substantial proportion of the more readily oxidizable solute at the surface of the implant while maintaining a metallic luster on the surface of the implant.

2. The hardened metallic medical implant of claim 1, wherein the metallic alloy of the implant body is selected from the group of alloys and metals consisting of Ti-6Al-4V, Ti—Mo, Ti—Al—Nb, Ti—Fe, Ti—V, Zr, Zr—Nb, Ti—Nb, Ti—Nb—Zr, Co—Cr—Mo, and Fe—Cr—Ni—Mo; and the more readily oxidizable metal solute is selected from the group consisting of tantalum, yttrium, hafnium, thorium, zirconium, chromium, niobium, and aluminum.

3. The hardened metallic medical implant of claim 1, wherein the implant body comprises a metal alloy having a composition of about 84 wt. % titanium, and about 15 wt. % niobium; and the metal solute is selected from the group consisting of tantalum, yttrium, zirconium, hafnium, chromium, and aluminum.

4. The hardened metallic medical implant of claim 1, wherein the metallic alloy implant body comprises about 74 wt. % titanium, about 13 wt. % niobium, and about 13 wt. % zirconium; and the metal solute is selected from the group consisting of hafnium, chromium, tantalum, yttrium, thorium, and aluminum.

5. The surface hardened metallic medical implant of claim 1, wherein the metallic alloy implant body comprises Ti-6Al-4V; and the metal solute is tantalum.

6. The surface hardened metallic medical implant of claim 1, wherein the metallic alloy implant body comprises Co—Cr—Mo alloy and the metal solute is selected from the group consisting of tantalum, aluminum, and yttrium.

7. The surface hardened metallic medical implant of claim 1, wherein the metallic alloy implant body comprises Fe—Cr—Ni—Mo alloy and the metal solute is selected from the group consisting of tantalum, aluminum, and yttrium.

8. The surface hardened metallic medical implant of claim 2, wherein the implant body has been further hardened by diffusion into the metallic alloy of the implant of an element selected from the group consisting of nitrogen, oxygen, and carbon.

9. A surface hardened metallic medical implant, the implant having a metallic alloy body with a surface, the body comprising:
   a metallic alloy, and less than about 2 wt. % of a metal solute that is more oxidizable than metallic components of the metallic alloy body, a substantial proportion of the metal solute at a depth of less than about 200 microns beneath the surface of the implant body being oxidized to strengthen and harden the surface of the implant to a hardness of about 40 Rockwell C, the solute being oxidized by a process comprising internally oxidizing solute near the surface of the implant body while maintaining a metallic luster on the surface of the implant.

10. The surface hardened metallic medical implant of claim 9, wherein the body comprises Co—Cr—Mo alloy.

11. The surface hardened metallic medical implant of claim 9, wherein the body comprises Ti-6Al-4V.

12. The surface hardened metallic medical implant of claim 9, wherein the body comprises Fe—Cr—Ni—Mo alloy.

13. The surface hardened metallic medical implant of claim 10, wherein the metal solute is selected from the group consisting of tantalum, aluminum, and yttrium.

14. The surface hardened metallic medical implant of claim 11, wherein the metal solute is tantalum.

15. A surface hardened metallic medical implant, the implant comprising:
   a surface hardened cobalt-chromium-molybdenum implant body with surface hardness greater than about 40 Rockwell C, the alloy comprising a hardened surface produced by a process comprising:
   (1) selecting a cobalt-chromium-molybdenum alloy containing from about 1 to about 2 wt. % tantalum, the tantalum being more internally oxidizable than other elements of the cobalt-chromium-molybdenum alloy implant body;
   (2) hardening the surface of the implant body by internal oxidation of a substantial proportion of the tantalum at the surface of the implant while maintaining a metallic luster on the surface of the implant.

16. A surface hardened metallic medical implant, the implant having a metallic alloy body with a surface, the body comprising:
   a cobalt-chromium-molybdenum alloy, and from about 1 to about 2 wt. % of tantalum as a metal solute, a substantial proportion of the tantalum at a depth of less than about 200 microns beneath surfaces of the implant body being oxidized to strengthen and harden the surface to a hardness of about 40 Rockwell C, the tantalum solute being oxidized by a process comprising internally oxidizing said solute near the surface of the implant body.

* * * * *